United States Patent [19]

Cowie

[11] Patent Number: 5,599,529
[45] Date of Patent: Feb. 4, 1997

[54] DISPERSIONS

[75] Inventor: Alan G. Cowie, Stockton on Tees, England

[73] Assignee: Tioxide Group PLC, United Kingdom

[21] Appl. No.: 530,536

[22] Filed: Sep. 20, 1995

Related U.S. Application Data

[63] Continuation of Ser. No. 566,318, Aug. 13, 1990, abandoned, which is a continuation of Ser. No. 197,280, May 23, 1988, abandoned.

[30] Foreign Application Priority Data

May 30, 1987 [GB] United Kingdom ............... 8712752

[51] Int. Cl.$^6$ ............................. A61K 7/42; C09C 1/36
[52] U.S. Cl. ................ 424/59; 106/436; 424/60; 424/400; 424/401; 514/937; 514/938
[58] Field of Search .................... 424/59, 60, 400, 424/401; 514/937, 938; 106/436

[56] References Cited

U.S. PATENT DOCUMENTS

| | | | |
|---|---|---|---|
| 3,579,310 | 5/1971 | Lewis et al. | 423/610 |
| 3,728,443 | 4/1973 | Berisford et al. | 423/610 |
| 3,923,968 | 12/1975 | Basque et al. | 423/610 |

FOREIGN PATENT DOCUMENTS

| | | | |
|---|---|---|---|
| 0703340 | 7/1982 | European Pat. Off. . | |
| 0214308 | 4/1985 | European Pat. Off. . | |
| 49-000450 | 1/1974 | Japan . | |
| 9000450 | 1/1974 | Japan | 424/59 |
| 0072833 | 6/1977 | Japan | 424/59 |
| 0124627 | 10/1978 | Japan | 424/59 |
| 54-073193 | 6/1979 | Japan . | |
| 87040292 | 12/1980 | Japan . | |
| 57-067681 | 4/1982 | Japan | 424/59 |
| 58-043912 | 3/1983 | Japan . | |
| 84015885 | 3/1983 | Japan . | |
| 0043912 | 3/1983 | Japan | 424/59 |
| 0062106 | 4/1983 | Japan . | |
| 58-062106 | 4/1983 | Japan . | |
| 0098009 | 6/1984 | Japan . | |
| 0172415 | 9/1984 | Japan | 424/59 |
| 59-223231 | 12/1984 | Japan . | |
| 60-186418 | 9/1985 | Japan . | |
| 61-097133 | 5/1986 | Japan . | |
| 61-215216 | 9/1986 | Japan . | |
| 458535A2 | 7/1979 | U.S.S.R. . | |
| 1256341 | 1/1969 | United Kingdom . | |
| 1387281 | 3/1975 | United Kingdom | 424/59 |
| 1479988 | 7/1975 | United Kingdom . | |
| 1541621 | 3/1979 | United Kingdom . | |

OTHER PUBLICATIONS

Hirosawa et al., "Paints for the Skin Coloring," Chem. Abst. (Dec. 1977), vol. 87, p. 300, Abstract 87:189306.

Primary Examiner—Shelley A. Dodson
Attorney, Agent, or Firm—Baker & Botts, L.L.P.

[57] ABSTRACT

Dispersions of titanium dioxide in various media have been known but there has been an increasing demand for the use of titanium dioxide as an absorber for UV light while remaining substantially transparent to visible light. Hitherto it has not been practical to prepare a high solids content oil dispersion of such material having an extremely high maximum extinction coefficient in the ultra violet range of wavelengths.

Such a dispersion has now been developed in an oil of particles of titanium dioxide having an average size from 0.01 to 0.15 micron and an organic dispersing agent in which dispersion the amount of said particles are such that the dispersion has a solid content greater than 40% by weight. The dispersion has a maximum extinction co-efficient in the ultra violet range of wavelengths of at least 40 liters per gram per cm.

28 Claims, No Drawings

DISPERSIONS

This application is a continuatin of application Ser. No. 07/566,318, filed Aug. 13, 1990, which is continuation of application Ser. No. 197,280 filed May 23, 1988, both abd.

This invention relates to dispersions of titanium dioxide particles and particularly to dispersions of these particles in an oil.

According to the present invention an oil dispersion comprises an oil, particles of titanium dioxide having an average size of from 0.01 to 0.15 micron and an organic dispersing agent for said particles, the amount of said particles being such that the dispersion has a solids content of greater than 40 percent by weight and said dispersion being substantially transparent to visible light and substantially absorbant to UV light so that the dispersion has a maximum extinction coefficient (E(max)) in the ultra violet range of wavelengths of at least 40 liters per gram per cm.

According to the invention also a method for the manufacture of an oil dispersion comprises milling in the presence of a particulate grinding medium particulate titanium dioxide in an oil and in the presence of an organic dispersing agent for said titanium dioxide in said oil in which the amount of said titanium dioxide is such that the dispersion has a solids content of greater than 40 percent by weight and continuing said milling for a period of time such that the particulate titanium dioxide has an average size of from 0.01 to 0.15 micron and that the dispersion obtained has a maximum extinction coefficient in the ultra violet range of wavelength of at least 40 liters per gram per cm.

The invention is a dispersion of the fine particle sized titanium dioxide dispersed in a high amount in an oil and is particularly directed to the use of an oil which is suitable for inclusion in a cosmetic product particularly useful as a preparation to protect skin against sun-burning or other damage associated with exposure to ultra violet radiation. Such materials are of increasing importance and use now since a greater number of people than ever are enjoying leisure activities in the outdoors and increasing their exposure to sun-light.

Generally speaking the particles of titanium dioxide in the oil dispersion have an average size of from 0.01 to 0.15 micron and where the particles are substantially spherical then this size will be taken to represent the diameter. However since the invention also encompasses the use of non-spherical particles then in such cases the size refers to the largest dimension. One preferred product is acicular in shape and has a ratio of largest dimension to the shortest dimension of from 8:1 to 2:1.

Most preferably the particles of titanium dioxide have an average size within the range 0.01 to 0.03 micron when they are substantially spherical in shape. For particles having an acicular shape then the average largest dimension preferably is within the range 0.02 to 0.1 micron.

Also it is preferred that the particles of titanium dioxide do have a narrow size distribution and the most preferred spherical particles have from 80 percent to 100 percent within the range 0.01 to 0.15 micron.

The titanium dioxide particles to be used to form the dispersions of the present invention can be anatase titanium dioxide, or rutile titanium dioxide or amorphous, and may be uncoated or coated as is desired with one or more oxides or hydrous oxide of e.g. aluminium, silicon, titanium, zirconium, magnesium or zinc. Preferably when the particles are coated then the coating is formed of an oxide or a hydrous oxide of aluminium and an oxide or hydrous oxide of silicon in a weight ratio of $Al_2O_3:SiO_2$ of at least 1.5 and not greater than 4.5 and preferably the ratio is within the range 2.0 to 3.5.

The actual amount of the coating present is such that the amount of oxide or hydrous oxide of aluminium when expressed as $Al_2O_3$ is from 1.0 to 30.0 weight percent based on weight of titanium dioxide and preferably from 5.0 to 20.0 weight per cent $Al_2O_3$ on weight of titanium dioxide. Consequently the amount of oxide or hydrous oxide of silicon will be that necessary to maintain the ratio of the amounts of coating oxides or hydrous oxides within the specified range and generally speaking the weight of oxide or hydrous oxide of silicon will be within the range 0.2 to 20.0 weight percent $SiO_2$ based on titanium dioxide and preferably from 1.5 to 7.0 weight percent.

If desired the particulate material may carry a coating of one or more organic materials such as an organic silicon compound e.g. a polymeric organic silicon compound. Other organic coating agents which may be present are the polyols, amines, or alkanolamines.

The particulate material of the present invention may be formed by any suitable process. Typical processes may involve hydrolysis of an appropriate titanium compound such as titanium tetrachloride or an organic or inorganic titanate or oxidation of an oxidisable titanium compound for example in the vapour state.

A typical process involves the preparation of a solution of a soluble titanium salt which is then hydrolysed to form hydrous titanium oxide. The solution can be that obtained in the so-called "sulphate" process for the manufacture of titanium dioxide pigment in which a titaniferous ore is digested with concentrated sulphuric acid and the digestion cake dissolved in water or dilute acid to produce a solution of titanyl sulphate. During the process additional process stages of classification and reduction are usually employed. Hydrolysis of the titanyl sulphate solution produces he precipitate of hydrous titania which is sometimes called "pulp". Soluble iron compounds remain in solution and after neutralisation and washing to an appropriate degree of impurity level the precipitated hydrous titania is treated to precipitate the specified chosen coating, if any, on the particulate product. If desired the hydrous titania can be treated with sodium hydroxide and subsequently hydrochloric acid to form an acicular titanium dioxide product.

Usually prior to coating of the particulate product it is preferred to mill the product to an appropriate particle size falling within that specified hereinbefore. Milling conveniently can be effected in a wet milling process employing a grinding medium such as sand which can be separated easily and effectively from the milled product. Milling, preferably, as carried out in the presence of a dispersing agent such as sodium silicate which provides the source of the coating hydrous silica deposited subsequently. Should another dispersant be used, for example, an organic dispersant, then the source of coating hydrous silica is added subsequently.

If desired the precipitated product is then treated to deposit the coating of, say, hydrous silica and hydrous alumina in the specified amounts and proportions. To an aqueous dispersion of the product containing a hydrolysable salt of aluminium and usually a silicate there is added a reagent which effects hydrolysis of the salt of aluminium and of the silicate to form hydrous alumina and hydrous silica. Typically aluminium sulphate can be the source of alumina or alkaline aluminate can be employed or indeed both an acidic aluminium salt and an alkaline solution of an aluminate can be added either together or sequentially.

Depending on the pH of the dispersion of the product hydrolysis and precipitation may require the addition of an alkali or an acid as the reagent. Preferably coating is effected by adding to an acid reacting dispersion of the product containing an alkali metal silicate an amount of aluminium sulphate followed by an amount of an alkali metal aluminate prior to the addition of a mineral acid such as sulphuric acid to effect formation and precipitation of hydrous alumina and adjustment of the pH of the dispersion to a value in the range 6 to 8, preferably pH 6.8 to 7.5.

The titanium dioxide product coated, or not, is separated from the aqueous dispersion in which it has been prepared and after washing is dried at an elevated temperature of say 70° C. to 110° C. In contrast to the usual "sulphate" process for the production of pigmentary titanium dioxide no calcination of hydrous titania is carried out. Consequently it may be that some of the titania used to prepare the product of the invention is present in a hydrous form even after drying.

Alternatively the particles of titania to be used in accordance with the present invention can be prepared by decomposition or hydrolysis of suitable titanium compounds. Typically high temperature hydrolysis of an organic titanium compound such as a titanium alkoxide can be used to produce the fine particle sized titania. Oxidation or hydrolysis in the vapour state of titanium halides under appropriate conditions can be also used to prepare the titania.

The products of the present invention have the property of absorbing UV light and transmitting visible light. This means that the products can find use in a wide variety of applications wherein it is important to maintain transparency to visible light while substantially preventing transmission of UV light to a surface. Cosmetics, sun-creams, plastics films and wood coating and other coating compositions are just a small number of applications for the products.

The particle absorbancy for UV light is expressed as a function of the amount of the uncoated particle and when expressed as an extinction coefficient is substantially independent of a medium in which the particles are dispersed. Generally speaking the dispersion of particles of the present invention have at least a maximum extinction coefficient E(max) when adequately dispersed of at least 40 liters per gram of uncoated product per cm in the ultra violet range of wavelengths. Preferably the dispersion has a maximum extinction coefficient E(max) within the range of 43 to 80.

The oil dispersions of the present invention are prepared by milling with a particulate grinding medium the titanium dioxide product coated, or not, with the chosen oil and a dispersing agent in the desired amount until the dispersion has the desired maximum extinction coefficient E(max) and the titanium dioxide product has the particle size within the range stated hereinbefore.

The oil can be any oil which is desirably present in the resultant dispersion but usually will be an oil which finds value in a cosmetic preparation. Such oils usually are the vegetable oils, for example, fatty acid glycerides, fatty acid esters and fatty alcohols with typical examples being sunflower oil (fatty acid triglyceride), castor oil, oleic and linoleic glycerides, saturated fatty acid di-esters e.g. octyl -dodecyl stearoyl stearate, oleyl alcohol, and isopropyl palmirate, pentaerythritol tetracaprylate/caprate, propylene glycol di-esters of coconut fatty acids and pentaerythritol tetraisostearate.

The mill which is employed to effect the grinding of the titanium dioxide product in the oil is one which uses a particulate grinding medium to grind the product. Such mills are bead mills equipped with one or more agitators and using sand or glass beads or ceramic beads or other particles as the particulate grinding medium. Particularly useful are those mills which operate at a high speed and depending on the size of mill a speed of the order of 2500 rev. per minute (r.p.m) is not unusual. For instance mills operating at a speed of from 1000 r.p.m to 6000 r.p.m are suitable. Agitator mills in which the tip speed of the agitator is up to and can exceed 10 meters/sec are of use. If desired the mill can be cooled. Also the dispersions can be pre-mixed using a high speed stirrer or the oil can be added to the mill initially and then the titanium dioxide and the organic dispersant co-added to the oil subsequently. After milling has been carried out for the required time the dispersion is separated from the grinding medium by screening through a narrow gap.

The dispersions of the present invention include an organic dispersing agent to promote the dispersion of the particulate titanium dioxide in the chosen oil. Many types of organic dispersing agent have been developed and are available for use in promoting the dispersion of particles in oily media. Typically the dispersing agent can be one having a formula X.Co.AR in which A is a divalent bridging group, R is a primary secondary or tertiary amino group or a salt thereof with an acid or a quaternary ammonium salt group and X is the residue of a polyester chain which together with the —CO-group is derived from a hydroxy carboxylic acid of the formula HO—R'—COOH. As examples of typical dispersing agents are those based on ricinoleic acid, hydroxystearic acid, hydrogenated castor oil fatty acid which contains in addition to 12-hydroxy -stearic acid small amounts of stearic acid and palmitic acid.

Dispersing agents based on one or more polyesters or salts of a hydroxycarboxylic acid and a carboxylic acid free of hydroxy groups can also be used. Compounds of various molecular weight can be used.

Other suitable dispersing agents are those monoesters of fatty acid alkanolamides and carboxylic acids and their salts based on 6-226 (un)saturated fatty acids. Alkanolamides are based ethanolamine, propanolamine or aminoethyl ethanolamine for example. Alternative dispersing agents are those based on polymers or copolymers of acrylic or methacrylic acids e.g. block copolymers of such monomers.

Other dispersing agents of similar general form are those having epoxy groups in the constituent radicals such as those based on the ethoxylated phosphate esters.

The dispersing agent can be one of those commercially referred to as a hyper dispersant specifically available as such.

When the dispersions of the invention are to be used in cosmetic or skin care preparations then it is desirable that the ingredients should have an acceptable level of toxicity and irritancy.

The quantity of the dispersing agent used depends on various factors but generally an amount of from 5 percent to 35 percent, preferably 5 to 20 percent by weight based on the weight of titanium dioxide will be used. The invention is illustrated in the following Examples.

EXAMPLE 1

Ilmenite was digested with concentrated sulphuric acid. The digestion cake obtained was dissolved in water to form a crude liquor containing iron and titanium sulphate and some suspended insoluble matter. Any iron present in the ferric form was reduced chemically prior to filtering insoluble matter. The liquor after any necessary crystallisation and filtration was concentrated by vacuum treatment and then hydrolysed to precipitate hydrous titanium dioxide by boiling and addition of any necessary reaction agent. The product on filtering was a pulp of uncoated hydrous $TiO_2$.

Four kilograms of the pulp so obtained was mixed with 5 liters of demineralised water. The pH of the diluted pulp was 1.9 and 375 ml of an aqueous solution of sodium hydroxide (containing 400 grams per liter NaOH) added to increase the pH to a value within the range 7.5 to 7.8. The dispersed pulp was filtered and the cake washed with 6.5 liters of demineralised water. The washed filter cake was then redispersed in 3 liters of demineralised water and the pH measured at a value of 8.4. Sulphuric acid (10%) (118 ml) was added to reduce the pH of the dispersion to 7.5 prior to filtering again. After washing the filter cake with 6.0 liters of demineralised water the solids content of the cake was 44.3% by weight.

677 grams of the filter cake (300 grams $TiO_2$) was diluted to a concentrati on of 100 grams per liter $TiO_2$ with demineralised water and mixed with sodium silicate in an amount equivalent to 5% by weight $SiO_2$ on weight of $TiO_2$ and milled in a sand mill for 2 hours after adjusting the pH of the dispersion to 10.0 to 11.5 with aqueous sodium hydroxide. The grinding medium was Ottowa sand and was removed from the milled dispersion at the end of the milling period by filtration.

The aqueous dispersion after removal of the sand having a pH of 8.9 was heated to 60° C. and maintained at this during the coating operation prior to any filtration taking place.

To the stirred dispersion aqueous aluminium sulphate solution (68 grams per liter $Al_2O_3$ equivalent) was added dropwise in an amount sufficient to introduce aluminium sulphate in an amount equivalent to 5% $Al_2O_3$ on weight of $TiO_2$ over a period of 60 minutes. Approximately 221 mls of the solution were added. After the addition has been completed the dispersion had a pH of 2.3 and was allowed to age for 30 minutes at 60° C. whilst stirring was maintained.

An alkaline solution of sodium aluminate (82 grams per liter $Al_2O_3$) was then added over a period of 60 minutes to the stirred dispersion in an amount sufficient to introduce the equivalent of 10% by weight $Al_2O_3$ on weight of $TiO_2$. Approximately 366 mls of the solution was found to have been added. The dispersion which had a pH of 11.6 was stirred at 60° C. for 45 minutes.

Sulphuric acid (10% was added to the aqueous dispersion to reduce the pH to 7.3. The neutralised dispersion was aged for 15 minutes whilst being stirred. The dispersion was filtered to produce a filter cake of the coated product which was then washed with 1 liter of demineralised water. The cake was redispersed in 1 liter of demineralised water, re-filtered and then washed again with demineralised water.

The product was dried at 110° C. overnight. The product was largely amorphous but containing some anatase titanium dioxide having an average size of 0.01 micron and being substantially spherical in shape with a coating of hydrous silica in an amount equivalent to 4.5 by weight $SiO_2$ on $TiO_2$ and hydrous alumina in an amount of 10.5% by weight $Al_2O_3$ on $TiO_2$ as determined by analysis of the product.

A sample of the dried product of the Example was tested in sunflower oil. 50 grams of the dry product was added with 70 mls of sunflower seed oil (density=0.93) and 2.5 grams of a dispersant being a polyhydroxy stearic acid known as Solsperse 3000 to a high speed bead mill (Eiger M-50-VSE) with 60 grams of 1 mm glass beads as grinding aid. The dispersion was milled for 3 hours. The solids content of the dispersion was 42% by weight.

After separation from the grinding aid a portion (0.1 gram) of the milled dispersion was diluted with n-hexane (100 ml). This diluted sample was then further diluted with n-hexane in the ratio sample:n-hexane of 1:19. The total dilution was 1:20,000.

The diluted sample was then exposed in a spectrometer (Beckman DU-50) with a 1 cm path length and the absorbance of UV and visible light measured. Extinction coefficients at two wave lengths were calculated from the equation A=E.c.l where A=absorbance, E=Extinction coefficient in liters per gram per cm, c=concentration in grams per liter and l=path length in cm.

The absorbance of UV and visible light was measured as described above and the extinction coefficient at the two wavelengths calculated as follows:

| E (524 nm) | E (308 nm) | E (max) | λ (max) |
| --- | --- | --- | --- |
| 1.5 | 27.2 | 49.6 | 245 |

EXAMPLE 2

Ilmenite was digested with concentrated sulphuric acid. The digestion cake obtained was dissolved in water to form a crude liquor containing iron and titanium sulphates and some suspended insoluble matter. Any iron present in the ferric form was reduced chemically prior to filtering insoluble matter. The liquor after any necessary crystallisation and filtration is concentrated by vacuum treatment and then hydrolysed to precipitate hydrous titanium dioxide by boiling and addition of any necessary reaction agent. The product on filtering was a pulp of uncoated hydrous $TiO_2$.

In the subseouent process any water added or used is taken to be demineralised water.

The pulp of the uncoated hydrous $TiO_2$ obtained was diluted to a concentration of 280 grams per liter $TiO_2$ and a sample amount of 2.5 liters taken and heated to 60° C. Aqueous sodium hydroxide solution containing 700 grams per liter NaOH in an amount of 1.5 liters was heated to 90° C. and then transferred to a reaction flask having a volume of 5 liters fitted with a condenser. The hot diluted pulp was added over a period of 30 minutes to the reaction flask whilst agitating the contents vigorously and the mixture temperature was held at 117° C. whilst agitating for a period of 2 hours after the addition had been completed. Cold water was added to quench the solution in the flask to 90° C. and to decrease the concentration of the product, sodium titanate, to 140 grams ($TiO_2$) per liter.

The amount of water added was approximately 20% of the total volume achieved. The contents were agitated for a further 15 minutes at this temperature of 90° C. prior to cooling to a temperature of 50° to 55° C. by the addition of a further amount of cold water which reduced the concentration of the product to about 80 to 90 grams $TiO_2$ per liter. The dispersion was filtered and the filter cake washed with warm water at a temperature of 50° C. to 60° C. so that the filtrate contained less than 1500 ppm $Na_2O$. The washed filter cake of sodium titanate was then reslurried in water to a concentration of 200 grams per liter $TiO_2$.

Two liters of the dispersed sodium titanate was added to a reaction flask having a volume of 6 liters and fitted with a condenser. The pH of the dispersion in the flask was reduced to a value within the range 2.8 to 3 1 by the addition of aqueous hydrochloric acid (30% w/w) and the mixture then heated to a temperature of 60° C. at the rate of 1° C. per minute. The pH of the mixture was rechecked and adjusted, if necessary, to a value within the range 2.8 to 3.1 by a further addition of the aqueous hydrochloric acid. The dispersion was held at this temperature for 30 minutes whilst agitated. A further quantity of hydrochloric acid was then added such that the volume added is 0.754 liters of 30% HCl acid per kilogram of $TiO_2$ in the dispersion such that the ratio of HCl/$TiO_2$ equals 0.26. The slurry was then boiled by heating to the boiling point over a period of 40 minutes and held at the boiling point for a period of 90 minutes whilst being agitated to hydrolyse the sodium titanate. The treated product was then quenched by addition of two liters of water and the dispersion had a pH value of 0.4. Sodium hydroxide solution at a concentration of 400 grams per liter NaOH was then added to neutralise the dispersion to a pH of 7.5 and approximately 460 ml of the aqueous sodium hydroxide was required. The dispersion was filtered and the filter cake washed with two liters of water. The washed filter cake was then redispersed with a further quantity of two liters of water and filtered again to produce a filter cake having a solids content of 34% by weight.

882 grams of the filter cake (300 grams $TiO_2$) was diluted to a concentration of 100 grams per liter $TiO_2$ with demineralised water and mixed with sodium silicate in an amount equivalent to 5% by weight $SiO_2$ on weight of $TiO_2$ and milled in a sand mill for 2 hours after adjusting the pH of the dispersion to 10.0 to 11.5 with aqueous sodium hydroxide The grinding medium was Ottowa sand and was removed from the milled dispersion at the end of the milling period by filtration.

The aqueous dispersion after removal of the sand having a pH of 9.1 was heated to 60° C. and maintained at this during the coating operation prior to any filtration taking place.

To the stirred dispersion aqueous aluminium sulphate solution (68 grams per liter $Al_2O_3$ equivalent) was added dropwise in an amount sufficient to introduce aluminium sulphate in an amount equivalent to 5% $Al_2O_3$ on weight of $TiO_2$ over a period of 60 minutes. Approximately 219 mls of the solution were added. After the addition has been completed the dispersion had a pH of 2.4 and was allowed to age for 30 minutes at 60° C. whilst stirring was maintained.

An alkaline solution of sodium aluminate (80 grams per liter $Al_2O_3$) was then added over a period of 60 minutes to the stirred dispersion in an amount sufficient to introduce the equivalent of 10% by weight $Al_2O_3$ on weight of $TiO_2$. Approximately 375 mls of the solution was found to have been added. The dispersion which had a pH of 11.8 was stirred at 60° C. for 45 minutes.

Sulphuric acid (10% was added to the aqueous dispersion to reduce the pH to 7.5. The neutralised dispersion was aged for 15 minutes whilst being stirred. The dispersion was filtered to produce a filter cake of the coated product which was then washed with 1 liter of demineralised water. The cake was redispersed in 1 liter of demineralised water, re-filtered and then washed again with demineralised water.

The product was dried at 110° C. overnight. The product was acicular rutile titanium dioxide having an average size of 0.02×0.10 microns with a coating of hydrous silica in an amount equivalent to 4.8% by weight $SiO_2$ on $TiO_2$ and hydrous alumina in an amount of 11.2% by weight $Al_2O_3$ on $TiO_2$ as determined by analysis of the product.

A sample of the dried product was tested in sunflower oil. 50 grams of the dry product was added with 70 mls of sunflower seed oil (density=0.93) and 5.0 gram of a dispersant being a polyhydroxy stearic acid known as Solsperse 3000 to a high speed bead mill (Eiger M-50-VSE) with 60 gram of 1 mm glass beads as grinding aid. The dispersion was milled for 3 hours.

After separation from the grinding aid a portion (0.1 gram) of the milled dispersion was diluted with n-hexane (100 ml). This diluted sample was then further diluted with n-hexane in the ratio sample:n-hexane of 1:19. The total dilution was 1:20,000.

The absorbance of UV and visible light was measured as described in Example 1 and the Extinction coefficient at the two wavelengths calculated as follows:

| E (524 nm) | E (308 nm) | E (max) | λ (max) |
| --- | --- | --- | --- |
| 4.0 | 42.3 | 43.9 | 285 |

EXAMPLE 3

The experiment described in Example 2 was repeated except that the product was coated with a hydrous oxide of silicon in an amount of 2% by weight $SiO_2$ and with a hydrous oxide of aluminium in an amount of 6% by weight $Al_2O_3$ on $TiO_2$ by changing the amounts appropriately of the coating reagents.

The product was formed as described in Example 1 into a dispersion in sunflower oil tested as in Example 1.

| E (524 nm) | E (308 nm) | E (max) | λ (max) |
|---|---|---|---|
| 2.9 | 49.0 | 51.3 | 292 |

EXAMPLE 4

The method described in Example 2 was repeated except that no coating was applied to the product.

The product was formed into a dispersion in isopropyl palmitare as the oil containing 44% by weight of the product and tested as described in Example 2.

| E (524 nm) | E (308 nm) | E (max) | λ (max) |
|---|---|---|---|
| 3.6 | 53.6 | 60.4 | 290 |

EXAMPLE 5

A solution of titanium tetrachloride in hydrochloric acid having an acid/titanium ratio (weight ratio) of 1.77 was prepared containing 200 grams per liter $TiO_2$ equivalent. An aqueous solution of sodium hydroxide (110 grams per liter) was prepared from carbonate free ingredients.

To a 3 liter glass flask fitted with a stirrer there was added 1203 ml of the aqueous sodium hydroxide solution and 400 ml of water (demineralised). To the stirred solution there was then added 400 mls of the titanium tetrachloride solution over a period of 15 minutes and during this period the stirrer speed was controlled at 100 rev. per minute. After the addition had been completed the temperature was raised from its initial value of 40°–45° C. to 82° C. at a rate of 1° C. per minute and the mixture was held at this temperature for a further 120 minutes while stirring continued. During the heating to the temperature of 82° C. the solution was observed to clear partially, normally at about 60°–70° C. as the titanium dioxide peptises and then re-precipitates.

After holding at 82° C. for 120 minutes the mixture was added to 2.5 liters of cold distilled water to quench the mixture then a further 5 liters of the water at 60° C. is added to the quenched mixture. Sodium hydroxide solution (110 grams per liter) was then added to the mixture to neutralise the mixture to a pH value of 7.5. The neutralised and flocculated mixture were allowed to settle, filtered and the cake washed with 2.5 liters of water by stirring prior to refiltering. The cake was washed again by re-slurrying with 2.5 liters of water and filtered to produce a cake having a solids content of 22% by weight.

The titanium dioxide in the cake was acicular and rutile having an average size of 0.01 to 0.05 microns.

A dispersion in sunflower oil was prepared as described in Example 1 containing 43% by weight of the product. The dispersion was tested and the following results obtained.

| E (524 nm) | E (308 nm) | E (max) | λ (max) |
|---|---|---|---|
| 0.20 | 49.0 | 79.6 | 270 |

EXAMPLE 6

The experiment described in Example 5 was repeated except that in this case the acicular titanium dioxide product obtained was coated with hydrous sil ica in an amount of 4% by weight and hydrous alumina in an amount of 12% by weight on weight of $TiO_2$ by a procedure similar to that described in Example 2.

A dispersion in sunflower oil was prepared as described in Example 1 and tested. The results are given below.

| E (524 nm) | E (308 nm) | E (max) | λ (max) |
|---|---|---|---|
| 0.4 | 35.0 | 51.5 | 280 |

EXAMPLE 7

A series of titanium dioxide products were prepared by the general procedure of Example 2 in which some were coated with hydrous silica and hydrous alumina but the majority uncoated.

Oil dispersions were prepared in various oils and at various solids contents. All were tested as described previously and the results are given in the following two Tables I and II. The results for uncoated products are given in Table I and those for coated products in Table II.

TABLE I

| % Solids | Oil | Dis-persant | % Disp. w/w | E(524) | E(308) | E(max) | λ(max) |
|---|---|---|---|---|---|---|---|
| 42 | 1 | a | 4.2 | 2.6 | 50.4 | 54.5 | 285 |
| 44 | 2 | " | 4.4 | 3.6 | 53.6 | 60.4 | 290 |
| 54 | 2 | " | 5.7 | 1.3 | 45.4 | 54.8 | 282 |
| 42 | 3 | " | 4.2 | 1.9 | 41.0 | 48.5 | 279 |
| 43 | 4 | " | 4.3 | 2.1 | 49.8 | 59.6 | 282 |
| 42 | 5 | " | 4.2 | 1.9 | 35.8 | 45.0 | 282 |
| 41 | 6 | " | 4.1 | 1.8 | 55.8 | 61.9 | 288 |
| 42 | 7 | " | 4.2 | 1.9 | 50.5 | 59.9 | 282 |
| 44 | 8 | " | 4.4 | 4.7 | 45.9 | 48.5 | 290 |
| 44 | 2 | b | 3.1 | 2.1 | 48.8 | 58.6 | 285 |
| 43 | 2 | c | 6.6 | 4.5 | 49.6 | 53.5 | 288 |

TABLE II

| Coating | | % | | | | | | | |
|---|---|---|---|---|---|---|---|---|---|
| SiO₂ (%) | Al₂O₃ (%) | % Solids | Oil | Dispersant | Disp. w/w | E(524) | E(308) | E(max) | λ(max) |
| 2.0 | 6.0 | 43 | 1 | a | 4.3 | 3.4 | 59.0 | 61.8 | 292 |
| 3.0 | 9.0 | " | " | " | " | 2.8 | 57.3 | 57.5 | 285 |
| 5.0 | 15.0 | " | " | " | " | 4.0 | 42.3 | 43.9 | 285 |

In the above Tables the oils used to prepare the dispersion were as follows:

| OIL | 1. | Sunflower oil (fatty acid triglyceride) |
|---|---|---|
| " | 2. | Isopropyl palmitate (Crodamol IPP) |
| " | 3. | Arachis oil (oleic and linoleic glyceride) |
| " | 4. | Octyl dodecyl stearoyl stearate (CERAPHYL 847) |
| " | 5. | Pentrerythritol tetracaprylate/caprate (CRODAMOL PC) |
| " | 6. | Propylene glycol diester of coconut fatty acid (CRODAMOL PTC) |
| " | 7. | Pentaerythritol tetraisostearate (CRODAMOL PTIS) |
| " | 8. | Oleyl alcohol (NOVOL) |

The dispersants used were as follows:

Dispersant a=polyhydroxystearic acid (Solsperse 3000) or (HYPERMER LP1)

b=polyhydroxycarboxylic acid (Solsperse 21000)

c=Ethoxylated phosphate mono ester (BRIPHOS C06M) of general formula $R(OCH_2CH_2)_nOP(OH)_2O$ in which R is cetyl/oleyl and n=6

EXAMPLE 8

The experiment described in Examples 5 and 6 was repeated to produce an uncoated titanium dioxide product and a product coated with hydrous oxide of silica (5% SiO₂) and a hydrous oxide of aluminium (15% Al₂O₃).

Oil dispersions at a solids content of 43% by weight were pepared using sunflower oil and dispersant "a". The products were tested as described in Example I and the results given in Table III.

TABLE III

| | % Solids | Oil | Dispersant | % Disp. w/w | E(524) | E(308) | E(max) | λ(max) |
|---|---|---|---|---|---|---|---|---|
| UNCOATED | 43 | 1 | a | 4.8 | 0.5 | 46.8 | 67.6 | 271 |
| COATED | " | " | " | 7.5 | 1.2 | 36.6 | 63.5 | 272 |

EXAMPLE 9

A sample of the first titanium dioxide dispersion (42% solids, uncoated, dispersant "a") referred to in Example 7 was prepared into a sunscreen composition (A) according to the following formulation.

| Item | | (A) % w/w |
|---|---|---|
| 1 | Polyglycol cetostearate (Tefose 1500) | 6 |
| 2 | Myristyl myristate (Crodamo) MM) | 1 |
| 3 | Titanium dioxide dispersion | 12.5 |
| 4 | Water | 74.3 |
| 5 | Carbomer (Carbopol 941) | 0.1 |
| 6 | Glycerin | 2 |

-continued

| Item | | (A) % w/w |
|---|---|---|
| 7 | KOH | 0.1 |
| 8 | Water | 5 |

The sunscreen composition was prepared in a beaker using as agitator a colloid mill (Silverson). Items 1, 2 and 3 were heated to 70° C. in the beaker and milled to produce a cream. Item 5 was mixed with items 4 and 6 in a separate beaker and heated to 70° C. and to this mixture the cream was added slowly whilst milling. After the addition had been completed the mixture was homogenised for a further 10 minutes. Item 7 was dissolved in item 8 and then added to the homogenised mixture and the rich lotion so obtained allowed to cool whilst stirring.

A further sunscreen composition (B) was prepared in a similar manner according to the following formulation.

| Item | B % w/w |
|---|---|
| 1 | 10 |
| 2 | 1 |
| 3 | 25 |
| 4 | to 100 |
| 5 | 0.1 |
| 6 | 2 |
| 7 | 0.1 |
| 8 | 5 |

The compositions were then tested to determine the sun protection factors (SPF) using the in vitro Luviset cast method described in detail by Dr. M. Stockdale in the International Journal of the Society of Cosmetic Scientists 9.1987.

The two compositions were applied to the Luviset casts at an application rate of 1.5 mg/cm². For compositions which do not interact with the Luviset cast the average of the zero time reading and the 10 minute reading is used. These readings are termed the weighted cast SPF's.

For the two sunscreen compositions the results were as follows

|  | A | B |
| --- | --- | --- |
| Weighted cast SPF | 6.0 | 7.3 |

EXAMPLE 10

Two sunscreen compositions C and D were prepared from the same titanium dioxide dispersion used in Example 9 according to the following formulation.

| Item | | C % w/w | D % w/w |
| --- | --- | --- | --- |
| 1 | Polyglycol cetostearate (Tefose 1500) | 10 | 15 |
| 2 | Titanium dioxide dispersion | 12.5 | 25 |
| 3 | Light liquid paraffin (WOM 14) | 2 | 4 |
| 4 | Polyglycol $C_{12}$-$C_{18}$ Triglycerides (Labrafil M2130 CS) | 3 | 5 |
| 5 | Stearic acid | 1 | 2 |
| 6 | Water | to 100 | 45 |
| 7 | Glycerin | 3 | 3 |

The susnscreens were prepared in a similar manner to Example 9 using a colloid mill (Silverson) by premixing items 1, 2, 3, 4 and 5. Items 6 and 7 were mixed in the separate beaker and the other mixed ingredients added.

A light cream of good cosmetic properties was obtained.

The products C and D were tested as described in Example 9 to determine the weighted cast SPF values.

Also the two compositions C and D were tested in vivo on humans according to the procedure laid down in Standard DIN 67501: 1984.

The following results were obtained.

|  |  | C | D |
| --- | --- | --- | --- |
| Weighted cast | SPF | 9.3 | 10.8 |
| IN VIVO | SPF | 10.2 | 11.6 |

These results clearly illustrate the excellent properties of the products.

EXAMPLE 11

A sample (X) of the coated titanium dioxide prepared in Example 2 but dispersed in oil 2 and dispersant "a" (43% solids), E(max)=43.9, was incorporated in a sunscreen composition E.

A sample (Y) of the dispersion of titanium dioxide obtained in Example 4 was incorporated in a sunscreen composition F.

The compositions had the following formulae

| Item | | E % w/w | F % w/w |
| --- | --- | --- | --- |
| 1 | Polyglycol cetostearate (Tefose 1500) | 10 | 10 |
| 3 | Light liquid paraffin (WOM 14) | 2 | 2 |
| 4 | Polyglycol $C_{12}$-$C_{18}$ Triglycerides (Labrafil M 2130 CS) | 3 | 3 |

-continued

| Item | | E % w/w | F % w/w |
| --- | --- | --- | --- |
| 5 | Stearic acid | 1 | 1 |
| 6 | Water | to 100 | to 100 |
| 7 | Glycerin | 3 | 3 |
| 2 | Titanium dioxide dispersion X | 13.5 |  |
|  | Titanium dioxide dispersion Y |  | 11.6 |

The sunscreen compositions were prepared similarly to those of Example 10 and they were tested to determine the weighted cast SPF values.

The results are given below.

|  |  | E | F |
| --- | --- | --- | --- |
| Weighted cast | SPF | 7.0 | 7.5 |

I claim:

1. A oil dispersion comprising an oil, particles of titanium dioxide having an average size of from 0.01 to 0.15 micron and an organic dispersing agent for said particles, the amount of said particles being such that the dispersion has a solids content of greater than 40 percent by weight and said dispersion being substantially transparent to visible light and substantially absorbant to UV light so that the dispersion has a maximum extinction coefficient (E(max)) in the ultra violet range of wavelengths of at least 40 liters per gram per cm.

2. An oil dispersion according to claim 1 in which the particles of titanium dioxide are substantially spherical.

3. An oil dispersion according to claim 1 in which the particles of titanium dioxide have an average size within the range 0.01 to 0.03 micron.

4. An oil dispersion according to claim 1 in which the particles of titanium dioxide are acicular in shape.

5. An oil dispersion according to claim 1 in which the particles are acicular and the average largest dimension of the said particles is within the range 0.02 to 0.1 micron.

6. An oil dispersion according to claim 1 in which from 80 percent to 100 percent of said particles have a size within the range 0.01 to 0.15 micron.

7. An oil dispersion according to claim 1 in which the particles of titanium dioxide are uncoated.

8. An oil dispersion according to claim 1 in which the particles of titanium dioxide are coated with one or more oxides or hydrous oxides of aluminium, silicon, titanium, zirconium, magnesium or zinc.

9. An oil dispersion according to claim 1 in which the particles of titanium dioxide are coated with a hydrous oxide of aluminium and a hydrous oxide of silicon in a weight ratio of $Al_2O_3$:$SiO_2$ of at least 1.5 and not greater than 4.5.

10. An oil dispersion according to claim 1 in which the titanium dioxide is coated with an amount of a hydrous oxide of aluminium of from 1.0 to 30.0 percent by weight as $Al_2O_3$ on weight of titanium dioxide and an amount of a hydrous oxide of silicon of from 0.2 to 20.0 percent by weight as $SiO_2$ on weight of titanium dioxide.

11. An oil dispersion according to claim 1 in which the oil is a vegetable oil.

12. An oil dispersion according to claim 1 in which the oil is selected from the class of oils consisting of fatty acid esters, fatty alcohols and saturated fatty acid di-esters.

13. An oil dispersion according to claim 1 in which the oil is selected from the class of oils consisting of sunflower oil, castor oil, oleic glyceride, linoleic glyceride, octydodecyl stearolyl stearate, oleyl alcohol, isopropyl palmirate, pentaerythritoltetracaprylate/caprate, propylene glycol di-ester of coconut fatty acids or pentaerythritol tetraisostearate.

14. An oil dispersion according to claim 1 in which the organic dispersing agent has the formula X—CO—AR, where A is a divalent bridging group, R is a primary, secondary or tertiary amino group or salt thereof with an acid or a quaternery ammonium salt group, and X is the residue of a polyester chain which, together with the —CO- group, is derived from a hydroxy carboxylic acid.

15. An oil dispersion according to claim 14 wherein the hydroxy carboxylic acid is selected from the group consisting of ricinoleic acid, hydroxystearic acid and hydrogenated castor oil fatty acid.

16. An oil dispersion according to claim 14 wherein said residue of a polyester chain also contains a carboxylic acid which is free of hydroxyl groups.

17. An oil dispersion according to claim 1 in which the organic dispersing agent comprises monoesters of fatty acid alkanolamides and carboxylic acids wherein the fatty acids have from about 6 to about 22 carbon atoms.

18. An oil dispersion according to claim 1 in which the organic dispersing agent is selected from the group consisting of polymers of acrylic acid, polymers of methacrylic acid and copolymers of acrylic and methacrylic acids.

19. An oil dispersion according to claim 14 wherein at least one of X and R contain an epoxide radical.

20. An oil dispersion according to claim 14 in which the organic dispersing agent is a polyhydroxy carboxylie acid.

21. An oil dispersion according to claim 1 in which the organic dispersing agent is an ethoxylated phosphate monoester.

22. A method for the manufacture of an oil dispersion which comprises milling particulate titanium dioxide in the presence of a particulate grinding medium in an oil and in the presence of an organic dispersing agent for said titanium dioxide in said oil in which the amount of said titanium dioxide is such that the dispersion has a solids content of greater than 40 percent by weight and continuing said milling for a period of time such that the particulate titanium dioxide has an average size of form 0.01 to 0.15 micron and that the dispersion obtained has a maximum extinction coefficient in the ultra violet range of wavelength of at least 40 liters per gram per cm.

23. A method according to claim 22 in which the mill operates at a speed of from 3500 revolutions per minute to 7000 revolutions per minute.

24. A method according to claim 22 in which the mill operates at a speed of the order of 5000 revolutions per minute.

25. A method according to claim 22 in which the said grinding medium is sand.

26. A method according to claim 22 in which the grinding medium is small glass beads.

27. A method according to claim 22 in which the ingredients to be mixed are pre-mixed prior to milling.

28. A method according to claim 22 in which the oil is added to the mill initially and then the particulate titanium dioxide and said dispersing agent added simultaneously to the mill during grinding.

* * * * *

(12) EX PARTE REEXAMINATION CERTIFICATE (9337th)
United States Patent
Cowie

(10) Number: US 5,599,529 C1
(45) Certificate Issued: Oct. 5, 2012

(54) DISPERSIONS

(75) Inventor: Alan G. Cowie, Stockton on Tees (GB)

(73) Assignee: ICI Uniqema Inc., New Castle, DE (US)

Reexamination Request:
No. 90/012,016, Nov. 18, 2011

Reexamination Certificate for:
Patent No.: 5,599,529
Issued: Feb. 4, 1997
Appl. No.: 08/530,536
Filed: Sep. 20, 1995

Related U.S. Application Data

(63) Continuation of application No. 07/566,318, filed on Aug. 13, 1990, now abandoned, which is a continuation of application No. 07/197,280, filed on May 23, 1988, now abandoned.

(30) Foreign Application Priority Data

May 30, 1987 (GB) .................................. 8712752

(51) Int. Cl.
*A61K 8/11* (2006.01)
*A61K 8/29* (2006.01)
*C01G 23/053* (2006.01)
*C01G 23/00* (2006.01)
*C08K 9/02* (2006.01)
*C08K 9/00* (2006.01)
*C09C 1/36* (2006.01)

(52) U.S. Cl. ............ 424/59; 106/436; 424/60; 424/400; 424/401; 514/937; 514/938

(58) Field of Classification Search ........................ None
See application file for complete search history.

(56) References Cited

To view the complete listing of prior art documents cited during the proceeding for Reexamination Control Number 90/012,016, please refer to the USPTO's public Patent Application Information Retrieval (PAIR) system under the Display References tab.

*Primary Examiner* — Evelyn Huang

(57) ABSTRACT

Dispersions of titanium dioxide in various media have been known but there has been an increasing demand for the use of titanium dioxide as an absorber for UV light while remaining substantially transparent to visible light. Hitherto it has not been practical to prepare a high solids content oil dispersion of such material having an extremely high maximum extinction coefficient in the ultra violet range of wavelengths.

Such a dispersion has now been developed in an oil of particles of titanium dioxide having an average size from 0.01 to 0.15 micron and an organic dispersing agent in which dispersion the amount of said particles are such that the dispersion has a solid content greater than 40% by weight. The dispersion has a maximum extinction co-efficient in the ultra violet range of wavelengths of at least 40 liters per gram per cm.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-28 is confirmed.

* * * * *